United States Patent [19]

Pukkinen et al.

[11] Patent Number: 5,435,985
[45] Date of Patent: Jul. 25, 1995

[54] HYDROGENATION CATALYST FOR USE IN A HYDROGEN PEROXIDE PROCESS, AND METHOD FOR THE PREPARATION THEREOF

[75] Inventors: Arto Pukkinen, Kempele; Lauri Heikkinen; Rauni Ruuska, both of Oulu, all of Finland

[73] Assignee: Kemira Oy, Espoo, Finland

[21] Appl. No.: 193,805

[22] Filed: Feb. 8, 1994

[30] Foreign Application Priority Data

Feb. 10, 1993 [FI] Finland .................. 930584

[51] Int. Cl.$^6$ .............. C01B 15/023; C07C 37/00
[52] U.S. Cl. .................. 502/303; 423/584; 423/588; 502/463; 502/313; 502/326; 502/304; 502/308; 502/309; 502/314; 502/315; 502/316; 568/771; 568/772
[58] Field of Search ............ 568/771, 772; 502/463, 502/262, 242; 423/584, 582, 588

[56] References Cited

U.S. PATENT DOCUMENTS

| | | | |
|---|---|---|---|
| 2,914,382 | 11/1959 | William et al. | 23/207 |
| 3,789,115 | 1/1974 | Matsumura et al. | 423/588 |
| 3,965,251 | 6/1976 | Shin et al. | 423/588 |
| 4,009,252 | 2/1977 | Izumi et al. | 423/584 |
| 4,219,661 | 8/1980 | Becker et al. | 560/24 |
| 4,521,531 | 6/1985 | Coates et al. | 502/242 |
| 4,769,500 | 9/1988 | Yui et al. | 568/772 |
| 5,071,634 | 12/1991 | Maunula et al. | 423/588 |

FOREIGN PATENT DOCUMENTS

| | | |
|---|---|---|
| 005226 | 11/1979 | European Pat. Off. |
| 009802 | 4/1980 | European Pat. Off. |
| 56816 | 4/1980 | Finland . |
| 82669 | 4/1991 | Finland . |
| 2277030 | 1/1976 | France . |
| 1951568 | 5/1970 | Germany . |
| 3538816 | 5/1987 | Germany . |
| 49-05120 | 1/1974 | Japan . |
| 49-005120 | 4/1974 | Japan . |
| 931221 | 5/1982 | U.S.S.R. . |

OTHER PUBLICATIONS

European Search Report dated Jun. 2, 1994 in European Appln. No. 94 30 0889.

Primary Examiner—Werren B. Lone
Attorney, Agent, or Firm—Marshall, O'Toole, Gerstein, Murray & Borun

[57] ABSTRACT

The invention relates to a hydrogenation catalyst for use in the preparation of hydrogen peroxide and to a method for the preparation of the catalyst. The hydrogenation catalyst contains in the main platinum group metal, of which more than 50 wt % is palladium. According to the invention, at least one additional metal is added to the platinum group metal.

10 Claims, No Drawings

HYDROGENATION CATALYST FOR USE IN A HYDROGEN PEROXIDE PROCESS, AND METHOD FOR THE PREPARATION THEREOF

A hydrogenation catalyst for use in a hydrogen peroxide process, and a method for the preparation thereof The invention relates to a hydrogenation catalyst for use in the production of hydrogen peroxide, the catalyst mainly (i.e., predominant containing platinum group metal, of which more than 50 wt % is palladium, to a method for the preparation of the catalyst, and to a hydrogenation process, based on the use of the catalyst, as part of a hydrogen production process.

In the production of hydrogen peroxide by the anthraquinone process, hydrogenation, oxidation and extraction stages succeed one another. Anthraquinone, or a derivative thereof, dissolved in organic solvents is hydrogenated in the presence of a catalyst to the corresponding hydroquinone. The hydroquinone is oxidized with oxygen, whereupon it regenerates to its prehydrogenation form, and simultaneously hydrogen peroxide is formed. The formed hydrogen peroxide is removed by aqueous extraction. The anthraquinone is recycled to hydrogenation.

The catalyst used in the hydrogenation is in the main palladium. Palladium is used either as such or attached to various supports. The most commonly known supports are aluminum oxide, carbon, and silica gel. In supported catalysts the concentration of Pd may vary between 0.1 wt % and 10 wt %.

A Raney nickel catalyst has also been used in the preparation of hydrogen peroxide. The palladium catalyst has reduced the share of nickel catalyst in use.

Although the amount of catalyst is not decreased in the chemical reaction, the catalyst nevertheless loses part of its activity in use. Spent catalyst which has lost its activity can be reactivated by regeneration. In the regeneration of catalyst, organic solvents, acids/bases, are used, followed by water treatments, vaporizations, and possibly drying and thermal treatments.

A catalyst can be in part reactivated a few times by the treatments mentioned above. Finally, a stage is reached at which regeneration is no longer useful. At that time the noble metal is recovered from the catalyst and a new catalyst is prepared.

Efforts have been made to increase, by various means, catalyst activity and the retention time of the activity. To a silica gel supported catalyst there have been added, in addition to Pd, also zirconium, thorium, hafnium, cerium, titanium and aluminum as an oxide, hydroxide or carbonate (EP patent publication 009802 and U.S. Pat. No. 4 521 531).

Alumina support has been impregnated with copper and silver compounds in addition to palladium. The metals have been reduced onto the support by a conventional method. The additive metals improve the selectivity of the catalyst in the preparation of hydrogen peroxide (JP patent 74 05 120).

It has been observed that a corroded alloy of nickel and aluminum, which additionally contains iron, chromium, molybdenum and copper, has catalytic properties in the hydrogenation of anthraquinone. It is claimed that the selectivity of the catalyst is high. It is used in the preparation of hydrogen peroxide (SU patent 931221).

The drawbacks of the catalysts with additives mentioned above include complicated regeneration, recovery of the noble metals, the use of a new support with impregnation, addition of additives, and reductions.

An object of the invention is to provide, for use in a hydrogen peroxide process, a hydrogenation catalyst which eliminates the deficiencies involved in the above-mentioned state-of-the-art catalysts. Thus the objective is to provide a catalyst the activity of which is high and which is durable. These requirements are fulfilled by the catalyst according to the invention. It is likewise an object of the invention to provide a method for the preparation of the catalyst and a process for the hydrogenation of anthraquinone or a derivative thereof, based on the use of the catalyst, as part of a process for the production hydrogen peroxide.

Accordingly, the invention provides a hydrogenation catalyst for use in the preparation of hydrogen peroxide by the anthraquinone process, comprising finely-divided metal particles which in the main comprise one or more platinum group metals, more than 50 wt. % thereof comprising palladium, with the particles further containing at least one additional metal selected from the group consisting of iron, chromium, nickel, titanium, zirconium, aluminum, cerium, lanthanum, manganese, and cobalt. The invention further provides a method for preparing such a catalyst in which suspensible, finely grained metal particles in the main comprising one or more metals of the platinum group, with over 50 wt. % of the platinum group metal being palladium, and further containing at least one additional metal as set forth above.

By using a platinum group metal catalyst to which the addition according to the invention had been made, a multiplication of activity was, surprisingly, achieved as compared with a conventional noble metal catalyst without the additives. Furthermore, the catalyst according to the invention retains its activity for a longer period at a higher level than does a catalyst not containing the additives. The catalyst according to the invention has the further advantage that its regeneration requirement is lower than that of conventional hydrogenation catalysts.

Metals suitable for this purpose include metals of the platinum group (Pt, Pd, Rh, Ir, Os, Ru) and mixtures thereof. The form of the metal in the preparation of the catalyst is not decisive. They can be used in metallic form or in metallic ion form. Palladium and platinum are suitable platinum group metals. An active catalyst is obtained by using as the platinum group metal palladium or a combination of palladium and platinum. In the combination of palladium and platinum the amount of palladium is over 50 % by weight of the total amount of the platinum group metals.

Certain transition metals or aluminum are used as the additive. Iron, chromium and nickel are preferred additional metals. Other additional metals which can be used include zinc, copper, cobalt, manganese, vanadium, titanium, zirconium, aluminum, cerium, and lanthanum.

The additive used may consist of one or several additional metals. In the preparation of the catalyst the additional metals may be used in the form of a metal, metal salt, or metal salt solution. The additional-metal concentrations may vary for each component within 0.01–3.0 wt. %, calculated from the total platinum group metal amount.

The hydrogenation catalyst according to the invention is prepared by adding a additional metal to a platinum group metal catalyst of which more than fifty weight per cent is palladium. The adding of the additional metal to the platinum group metal takes place, for example, by precipitation from a solution. Alternatively, it is possible to use, for example, methods based on impregnation. In addition, the additional metal can be precipitated at high temperatures by using conventional precipitation methods or, for example, the plasma technique.

The metal catalyst particles preferably consist essentially of one or more noble metals and one or more transition metals, i.e. other elements, if any, are preferably present in the catalyst only as impurities in trace amounts.

The hydrogenation catalyst is prepared from a solution by dissolving in an acid a platinum group-metal containing catalyst of which more than fifty weight per cent is palladium and which may be in the form of either a salt or a metal. Platinum group metal in the form of a salt may be slurried in water before being dissolved in acid. One or more additional metal is added to the obtained acid solution. The additional metal may be as a metal, as a metal salt, or as a metal salt solution.

The temperature of the solution may vary between 10° and 100° C. The solution is neutralized with an alkaline material, for example with soda lye or potassium lye.

The platinum group metal is reduced, at which time the additional metal is coprecipitated. After the precipitation the pH will be between 6.5 and 10. The catalyst is obtained in the precipitation in the form of finely-divided metal particles having a particle size within the range of 1-100 $\mu$m.

The catalyst is washed clean of the mother liquor by means of water. The washed catalyst may be dried or transferred to an organic solvent medium environment or into a working solution medium before being tested and used.

A platinum group metal, such as palladium, used in metal form may be previously used metal or unused. Palladium in salt form may be any palladium-containing salt, e.g. halide, nitrate, or sulfate. Likewise, the additional-metal salt may comprise or consist of any of the salts mentioned above, for example nitrates, halides and sulfates. It is also possible to use metallic additional metals.

Acids suitable for the dissolving of platinum group metals include strong acids, in particular hydrochloric acid and nitric acid. The acid or the acid mixture is used in excess of the stoichiometric amount. In addition, hydrogen peroxide may be used, when necessary. The acid solution containing noble metal is diluted to a suitable concentration of 1-50 g/l before the adding of the additional metals. The additional metal components may be used in either the same proportion or in different proportions to the platinum group metal. The concentrations may vary, for each component, within 0.01-3.0 wt %, calculated from the total platinum group metal amount.

The reduction can be carried out by using a reducing agent suitable for the reduction of the platinum group metals, such as formaldehyde, formic acid, hydrogen, hydrazine, or sodium borohydride.

Hydrogenation catalysts according to a preferred embodiment are obtained by adding iron, chromium or nickel to palladium. It is also possible to use iron, chromium, or iron and nickel, or chromium and nickel. A particularly active hydrogenation catalyst is obtained when small concentrations of all of the three components are simultaneously mixed with the palladium.

The concentration range of the additional-metal components is limited separately for each additional metal component to 0.01-3.0 wt %. Beyond this concentration range the number of small particles will be too high. Additives even as such decrease and embrittle the palladium black particle, which in turn contributes to the increase of activity, but also small separate particles of additional-metal compounds cause a disadvantage both during the preparation according to the invention and during use.

The total amount of transition metal(s) in the catalyst preferably is no more than 3.0 wt. % of the amount of noble metal(s) in the catalyst. Thus, the catalyst preferably comprises at least 97.0 wt. % noble metal(s) and up to 3.0 wt. % transition metal(s).

The hydrogenation of anthraquinone or its derivatives is carried out by means of hydrogen or a hydrogen-containing gas in a working solution in which the finely-divided catalyst is suspended. As the solvent in the working solution it is possible to use organic solvents comprising or consisting of one or more components. Suitable solvents or suitable components of the solvent include aromatic hydrocarbons, which dissolve the anthraquinone, and more polar solvents, which retain the forming anthrahydroquinone in the solution. Suitable are, for example, secondary alcohols, trialkyl phosphates, 2,6-dialkylcyclohexanone, mono- and diacetyl benzophenone and triacetyl benzenes, tetralkyl urea compounds, amides and caprolactams.

In the following examples, catalyst activity was tested in a working solution containing 2-ethylanthraquinone 100 g/l and catalyst 0.5 g/l, in an organic solvent mixture made up of an aromatic hydrocarbon and organic phosphate. The testing was carried out in an autoclave under a pressure of three bar at a temperature of 50° C., with a hydrogenation time of five minutes. The $H_2O_2$ concentration was determined on the oxidized working solution. All percentages are based on weight.

EXAMPLE 1

Palladium chloride (200 g) was dissolved in a 33-percent hydrochloric acid (250 ml), and the solution was diluted to 10 liters. Aqueous solutions containing metal components were prepared from $FeCl_3.6H_2O$, $CrCl_3.6H_2O$ and $NiCl_2.6H_2O$ salts. The metal component concentration in the solutions was 1 g/l. That the components remained in the solutions was ensured by means of a small addition of hydrochloric acid (2 ml/l 33% HCl). 4.0 ml of an iron salt solution was added to 600 ml of the Pd solution. The pH of the solution was raised to approximately three by means Of lye before the adding of formic acid, which was used as the reducing agent (1.5× the stoichiometric amount in proportion to palladium). When the pH was increased with lye to approximately 9, the Pd was reduced and the additive metal is coprecipitated. The catalyst was prepared under a nitrogen shield gas. The catalyst is washed with water and is transferred from the aqueous medium to a working solution or to the solvent part of the working solution before the testing. The catalyst was tested as described above. The hydrogen peroxide yield obtained by means of the catalyst under the testing conditions was 15.7 g $H_2O_2$/g catalyst.

EXAMPLE 2

A catalyst was prepared in accordance with Example 1, except that no metal salt solution was added. The hydrogen peroxide yield obtained by means of the catalyst was 7.8 g $H_2O_2$/g catalyst.

EXAMPLE 3

A catalyst was prepared as in Example 1, but the additive-metal component was not added in the form of a solution but as a solid salt. The salt used was $FeCl_2 \cdot 6H_2O$. 90.5 mg of ferri-chloride was added per 600 ml of the Pd solution. The hydrogen peroxide yield obtained by means of the catalyst was 11.6 g $H_2O_2$/g catalyst.

EXAMPLE 4

A palladium black catalyst (0.068 mol) which had been used for the hydrogenation of anthraquinone was slurried in water and was dissolved in 55 ml of a 33-percent hydrochloric acid. 7 ml of a 50-% hydrogen peroxide was used as an auxiliary in the dissolving. In other respects the catalyst was prepared as in Example 1. Iron, which was used as the additive metal, was added in the form of an iron chloride solution according to Example 1, in an amount of 39.9 ml. The hydrogen peroxide yield obtained by means of the catalyst was 10.1 g $H_2O_2$/g catalyst.

EXAMPLE 5

A Pd catalyst (0.068 mol Pd) which had been used for the hydrogenation of anthraquinone was dissolved in 103 ml of a 30 percent $HNO_3$. In other respects the preparation of the catalyst was as in Example 1, but the above solution was used instead of a Pd chloride solution, and iron was added in metal form in an amount of 52.5 mg. The hydrogen peroxide yield obtained by means of the catalyst prepared was 12.2 g $H_2O_2$/g catalyst.

EXAMPLE 6

A palladium black catalyst was dissolved as in Example 4. The preparation was in other respects the same as in Example 1, but the reduction was carried out by means of formaldehyde (1.5× the stoichiometric amount in proportion to palladium) instead of formic acid, and 2.2 ml of a chromium salt solution was added instead of the iron salt solution. The amount of chromium added must be 10% more than the Cr concentration desired for the catalyst. The chromium salt solution was prepared in the manner according to Example 1. The hydrogen peroxide yield obtained by means of the catalyst was 12.9 g $H_2O_2$/g catalyst.

EXAMPLE 7

A catalyst was prepared as in Example 1, but instead of an iron salt solution, 15.1 ml of a chromium salt solution was added to the solution. The hydrogen peroxide yield obtained by means of the catalyst was 13.3 g $H_2O_2$/g catalyst.

EXAMPLE 8

A catalyst was prepared as in Example 7. The chromium salt solution was added in an amount of 20.6 ml. The hydrogen peroxide yield obtained by means of the catalyst was 13.3 g $H_2O_2$/g catalyst.

EXAMPLE 9

A catalyst was prepared as in Example 4, but 22.1 mg of chromium metal instead of an iron salt was added to the solution; the chromium metal was allowed to dissolve in the hydrochloric acid solution before the subsequent stage. The hydrogen peroxide yield obtained by means of the catalyst was 12.0 g $H_2O_2$/g catalyst.

EXAMPLE 10

A catalyst was prepared as in Example 1, but 0.8 ml of a nickel chloride solution instead of an iron salt solution was added to the solution. The hydrogen peroxide yield obtained by means of the catalyst was 11.8 g $H_2O_2$/g catalyst.

EXAMPLE 11

A catalyst was prepared as in Example 10, but the nickel chloride solution was added in an amount of 2.0 ml instead of 0.8 ml. The hydrogen peroxide yield obtained by means of the catalyst was 11.4 g $H_2O_2$/g catalyst.

EXAMPLE 12

A catalyst was prepared as in Example 11, but the nickel chloride solution was added in an amount of 4.2 ml instead of 2.0 ml. The hydrogen peroxide yield obtained by means of the catalyst was 11.4 g $H_2O_2$/g catalyst.

EXAMPLE 13

A catalyst was prepared as in Example 5, but 7.0 mg of nickel metal instead of iron was used. It was observed that the Ni metal had dissolved before the subsequent catalyst preparation stages. The hydrogen peroxide yield obtained by means of the catalyst was 10.8 g $H_2O_2$/g catalyst.

EXAMPLE 14

A catalyst was prepared as in Example 13, but nickel was added in an amount of 12.3 mg instead of 7.0 mg, and the reduction was carried out by means of formaldehyde as in Example 6. The hydrogen peroxide yield obtained by means of the catalyst was 11.4 g $H_2O_2$/g catalyst.

EXAMPLE 15

A catalyst was prepared as in Example 1, but this time two salt solutions were added to the Pd chloride solution: 38.8 ml of an iron chloride solution and 12.8 ml of a nickel chloride solution. The hydrogen peroxide yield obtained by means of the catalyst was 12.3 g $H_2O_2$/g catalyst.

EXAMPLE 16

A catalyst was prepared as in Example 4, but the additives used were 34.5 ml of an iron chloride solution and 7.1 ml of a nickel chloride solution. A measurement showed that the hydrogen peroxide yield obtained by means of the catalyst was 16.8 g $H_2O_2$/g catalyst.

EXAMPLE 17

A catalyst was prepared as in Example 1, but the iron and chromium used as additives were added as metals. Iron was added in an amount of 52.5 mg and chromium in an amount of 18.2 mg. The metals were allowed to dissolve in the Pd salt solution before the subsequent preparation stages. A measurement showed that the hydrogen peroxide yield obtained by means of the catalyst was 14.6 g $H_2O_2$/g catalyst.

EXAMPLE 18

A catalyst was prepared in accordance with Example 4. Iron chloride solution was used in an amount of 33 ml and chromium chloride solution in an amount of 22.1 ml. The hydrogen peroxide yield obtained by means of the catalyst was 12.2 g $H_2O_2$/g catalyst.

EXAMPLE 19

By dissolving nickel chloride and chromium chloride in water and by adding 2 ml of a strong hydrochloric acid per a one-liter batch, a solution was prepared having a Cr concentration of 3.3 g/l and a Ni concentration of 1.8 g/l. A catalyst was prepared as in Example 1, but the additive metals were batched in the form of the above solution (7 ml) into the palladium chloride solution. The hydrogen peroxide yield obtained by means of the catalyst was 11.0 g $H_2O_2$/g catalyst.

EXAMPLE 20

A catalyst was prepared in accordance with Example 4, except that the adding of the iron solution was omitted and 20.6 ml of a chromium chloride solution and 6.9 ml of a nickel chloride solution were added in its stead. The hydrogen peroxide yield obtained by means of the catalyst was 13.1 g $H_2O_2$/g catalyst.

EXAMPLE 21

A catalyst was prepared as in Example 1, but this time three metal components were added. The metal components were added as chloride solutions according to Example 1: iron solution in an amount of 19.4 ml, chromium solution 14.3 ml, and nickel solution 21 ml. The hydrogen peroxide yield measured for the catalyst was 12.0 g $H_2O_2$/g catalyst.

EXAMPLE 22

Used palladium catalyst was dissolved as in Example 5. The preparation was in other respects in accordance with Example 1. The iron, chromium and nickel were added as solutions in accordance with Example 1: iron solution in an amount of 33.8 ml, chromium solution 22.1 ml, and nickel solution 7.1 ml. The hydrogen peroxide yield measured for the catalyst was 27.5 g $H_2O_2$/g catalyst.

EXAMPLE 23

Used palladium catalyst was dissolved as in Experiment 4. The preparation was in other respects as in Example 1. Iron, chromium and nickel were added in the form of solutions according to Example 1. Iron solution was added in an amount of 19.4 ml, chromium solution 12.4 ml, and nickel solution 3.9 ml. The hydrogen peroxide yield measured for the catalyst was 15.0 g $H_2O_2$/g catalyst.

EXAMPLE 24

A catalyst was prepared as in Example 6, except that chromium chloride solution was now added in an amount of 7.3 ml, and additionally iron chloride solution according to Example 1 was added in an amount of 12.2 ml and nickel chloride solution in an amount of 2.8 ml. The hydrogen peroxide yield obtained for the catalyst in a test measurement was 14.2 g $H_2O_2$/g catalyst.

EXAMPLE 25

A catalyst was prepared as in Example 1. Iron was added as a metal in an amount of 6.1 g, deviating from Example 1, and the other components, chromium and nickel, were added in the form of chloride solutions in accordance with Example 1. The chromium-containing solution was added in an amount of 1.3 ml, and the nickel-containing solution in an amount of 0.7 ml. The hydrogen peroxide yield measured for the catalyst was 12.5 g $H_2O_2$/g catalyst.

EXAMPLE 26

A catalyst was prepared in accordance with Example 4. The iron chloride solution according to Example 1 was now added in an amount of 3.3 ml and the chromium and nickel solutions each in an amount of 4 ml, diluted 1:10 from the solutions of Example 1. The hydrogen peroxide yield measured for the catalyst was 13.1 g $H_2O_2$/g catalyst.

EXAMPLE 27

From iron chloride, chromium chloride and nickel chloride 1 liter of a solution was prepared which contained 2.7 g Fe, 1.7 g Cr, and 0.6 g Ni. That the solution remained in the form of a solution was ensured by making the solution acid by means of 2 ml of a strong, 33-percent hydrochloric acid. A catalyst was prepared in accordance with Example 4. The additive metals were batched by adding the above solution in an amount of 10 ml. The hydrogen peroxide yield measured for the catalyst was 22.4 g $H_2O_2$/g catalyst.

EXAMPLE 28

A catalyst was prepared from a palladium chloride solution as in Example 1. Iron in an amount of 23.7 mg was added in metal form to the solution, the chromium and nickel were added as chloride solutions according Example 1. Chromium solution was added in an amount of 10.3 ml and nickel solution in an amount of 4.8 ml. The hydrogen peroxide yield measured for the catalyst was 9.1 g $H_2O_2$/g catalyst.

EXAMPLE 29

A catalyst was prepared as in Example 6, but the iron, chromium and nickel were added in solid form, as chloride salts containing six molecules of water of crystallization: ferrichloride 104.5 mg, chromium(III) chloride 34.4 mg, and nickel(II) chloride 16.5 mg. The hydrogen peroxide yield measured for the catalyst was 11.0 g $H_2O_2$/g catalyst.

EXAMPLE 30

A catalyst was prepared as in Example 5. Iron in metal form was this time added in an amount of 28.8 mg, chromium was added as chromium(III) chloride (cf. Example 29) 65 mg, and nickel in metal form 5.7 mg. The hydrogen peroxide yield measured for the catalyst was 10.8 g $H_2O_2$/g catalyst.

EXAMPLE 31

A catalyst was prepared as in Example 1. The amount of iron-containing solution added was 3.6 ml, of chromium-containing solution 13.4 ml, and of nickel-containing solution 48 ml. The hydrogen peroxide yield measured for the catalyst was 14.8 g $H_2O_2$/g catalyst.

EXAMPLE 32

From $FeCl_3.6H_2O$, $CrCl_3.6H_2O$ and $NiCl_2.6H_2O$, one liter of a solution was prepared into which was weighed 83.6 g of the iron compound, 21.0 g of the chromium salt, and 8.7 g of the nickel compound. A catalyst was prepared according to Example 1, but the additive component was batched by adding 10 ml of the above solution. The hydrogen peroxide yield measured for the catalyst was 19.6 g $H_2O_2$/g catalyst.

EXAMPLE 33

540 ml of the palladium chloride solution according to Example 1 was taken, and 0.6 g of platinum was added to it as a $H_2PtCl_6.6H_2O$ compound in an amount of 1.6 g. In other respects the catalyst was prepared as in Example 1. The iron, chromium and nickel were added as solutions according to Example 1, iron-containing solution in an amount of 8.6 ml, chromium-containing solution 5.5 ml, and nickel-containing solution 6.5 ml. The hydrogen peroxide yield measured for the catalyst was 14.8 g $H_2O_2$/g catalyst.

EXAMPLE 34

A catalyst was prepared as in Example 33. To the palladium-platinum chloride solution was added 10.8 ml of a solution which had been prepared as in Example 1 but had a chromium concentration 10 times that in the chromium solution of Example 1. The hydrogen peroxide yield measured for the catalyst was 15.1 g $H_2O_2$/g catalyst.

To a palladium-containing acid solution (Pd2+) was added one or more additional metals as salt solutions. The pH of the solution was raised to approximately three by means of lye, before the adding (1.5× the stoichiometric amount in proportion to the palladium) of the formic acid which was used as the reducing agent. When the pH was raised by means of lye to approximately 9, the Pd was reduced and the additive metal coprecipitated. The catalyst was prepared under a shield gas of nitrogen. The catalyst was washed with water and was transferred from the aqueous medium to the working solution or to the solvent part of the working solution before the testing. The catalyst was tested as described above. The results are shown in the following table.

| Example No. | Ti ppm | Zr ppm | Al ppm | Ce ppm | La ppm | Mn ppm | Co ppm | H2O2 yield g/g cat. |
|---|---|---|---|---|---|---|---|---|
| 35 | 40 | | | | | | | 7.81 |
| 36 | 60 | | | | | | | 11.16 |
| 37 | 490 | | | | | | | 13.95 |
| 38 | 1100 | | | | | | | 14.32 |
| 39 | 3200 | | | | | | | 17.48 |
| 40 | 5650 | | | | | | | 19.53 |
| 41 | 8900 | | | | | | | 26.04 |
| 42 | 14800 | | | | | | | 18.60 |
| 43 | | 320 | | | | | | 9.30 |
| 44 | | 350 | | | | | | 11.16 |
| 45 | | 420 | | | | | | 12.65 |
| 46 | | 850 | | | | | | 11.72 |
| 47 | | 2100 | | | | | | 13.76 |
| 48 | | 5700 | | | | | | 16.55 |
| 49 | | 11000 | | | | | | 25.67 |
| 50 | | 19000 | | | | | | 26.04 |
| 51 | | | <400 | | | | | 7.81 |
| 52 | | | 770 | | | | | 13.58 |
| 53 | | | 2200 | | | | | 19.72 |
| 54 | | | 3700 | | | | | 12.09 |
| 55 | | | 6100 | | | | | 11.53 |
| 56 | | | 13800 | | | | | 21.20 |
| 57 | | | | <10 | | | | 7.81 |
| 58 | | | | 100 | | | | 11.35 |
| 59 | | | | 270 | | | | 9.11 |
| 60 | | | | 560 | | | | 7.81 |
| 61 | | | | 1950 | | | | 8.74 |
| 62 | | | | 3000 | | | | 13.39 |
| 63 | | | | | 90 | | | 6.51 |
| 64 | | | | | 300 | | | 8.56 |
| 65 | | | | | 700 | | | 9.49 |
| 66 | | | | | 2900 | | | 9.30 |
| 67 | | | | | 4800 | | | 9.67 |
| 68 | | | | | | 550 | | 7.44 |
| 69 | | | | | | 1100 | | 6.88 |
| 70 | | | | | | 3500 | | 6.88 |
| 71 | | | | | | 6300 | | 6.88 |
| 72 | | | | | | | 640 | 7.63 |
| 73 | | | | | | | 1300 | 12.09 |
| 74 | | | | | | | 3800 | 23.62 |
| 75 | | | | | | | 6500 | 26.04 |
| 76 | 1250 | 1100 | | | | | | 5.39 |
| 77 | 3800 | 2900 | | | | | | 5.39 |
| 78 | 1100 | | 820 | | | | | 8.00 |
| 79 | 3300 | | 3500 | | | | | 20.83 |
| 80 | 4800 | | 6100 | | | | | 15.62 |
| 81 | 1200 | | | 2200 | | | | 10.23 |
| 82 | 3500 | | | 4800 | | | | 17.67 |
| 83 | 5700 | | | 10000 | | | | 14.88 |

-continued

| Example No. | Ti ppm | Zr ppm | Al ppm | Ce ppm | La ppm | Mn ppm | Co ppm | H2O2 yield g/g cat. |
|---|---|---|---|---|---|---|---|---|
| 84 | | 1000 | <400 | | | | | 9.67 |
| 85 | | 3300 | 4300 | | | | | 14.88 |
| 86 | | 640 | | 690 | | | | 10.60 |
| 87 | | 2300 | | 2700 | | | | 16.18 |
| 88 | | 10000 | | 7700 | | | | 20.83 |
| 89 | | | <400 | 420 | | | | 8.18 |
| 90 | | | 3200 | 2300 | | | | 21.95 |
| 91 | | | 2700 | 4450 | | | | 15.81 |
| 92 | | | 2000 | | 1100 | | | 14.14 |
| 93 | | | 1500 | | 2700 | | | 23.25 |
| 94 | | | 2700 | | 4700 | | | 23.81 |
| 95 | 1100 | 1200 | <400 | | | | | 13.02 |
| 96 | 3700 | 3200 | 1900 | | | | | 16.93 |
| 97 | 6500 | 5300 | 4300 | | | | | 24.55 |
| 98 | 7200 | | 1900 | | 15600 | | | 25.11 |

The method according to the invention is not limited to the embodiment examples presented above; it can be varied within the scope defined by the accompanying patent claims. The essential idea is that the adding of the additional metal is carried out in such a way that the additional metal will become mixed with the platinum group metal.

We claim:

1. A hydrogenation catalyst for use in the preparation of hydrogen peroxide by the anthraquinone process, the catalyst comprising finely-divided metal particles which in the main comprise one or more platinum group metal, more than 50 wt. % of the platinum group metal being palladium, said particles further containing at least one additional metal selected from the group consisting of iron, chromium, nickel, titanium, zirconium, aluminum, cerium, lanthanum, manganese, and cobalt.

2. A hydrogenation catalyst according to claim 1, wherein the platinum group metal consists of palladium.

3. A hydrogenation catalyst according to claim 1, wherein the platinum group metal comprises palladium and platinum.

4. A hydrogenation catalyst according to claim 1, wherein the amount of each said additional metal in the catalyst is approximately 0.01–3.0 wt. % of the amount of the platinum group metal.

5. A method for the preparation of a hydrogenation catalyst intended for the production of hydrogen peroxide by the anthraquinone process, in which method suspensible, finely-grained metal particles are formed which in the main comprise one or more metals of the platinum group, over 50 wt. % of the platinum group metal being palladium, and, also contain at least one additional metal selected from the group consisting of iron, chromium, nickel, titanium, zirconium, aluminum, cerium, lanthanum, manganese, and cobalt.

6. A method according to claim 5, wherein the platinum group metal consists of palladium.

7. A method according to claim 5, wherein the platinum group metal comprises palladium and platinum.

8. A method according to claim 5, wherein the amount of each said additional metal in the catalyst is approximately 0.01–3.0 wt. % of the amount of the platinum group metal.

9. A method according to claim 5, wherein said additional metal is introduced into a platinum group metal solution, from which the metals are precipitated as finely-divided particles.

10. A method according to claim 9, wherein the additional metal is added in the form of a metal, a metal salt, or a metal salt solution to the platinum group metal solution.

* * * * *